United States Patent [19]

Niemeijer

[11] 4,392,493
[45] Jul. 12, 1983

[54] TATTOOING APPARATUS

[75] Inventor: Halbe J. Niemeijer, Assen, Netherlands

[73] Assignee: Dawsonville Corp., N.V., Curacao, Netherlands Antilles

[21] Appl. No.: 184,462

[22] Filed: Sep. 5, 1980

[30] Foreign Application Priority Data

Sep. 6, 1979 [NL] Netherlands ................. 7906689

[51] Int. Cl.$^3$ ............................................ A61D 7/00
[52] U.S. Cl. .................................. 128/316; 81/9.22; 101/26; 101/19
[58] Field of Search .................. 128/316, 330; 81/9.22; 101/26, 30, 19, 24; 40/300

[56] References Cited

U.S. PATENT DOCUMENTS

| 1,378,166 | 5/1921 | Amoedo . | |
|---|---|---|---|
| 2,884,853 | 5/1959 | Cantoni | 101/112 |
| 4,214,490 | 7/1980 | Chizek | 81/9.22 |
| 4,230,001 | 10/1980 | Noll et al. | 81/9.22 |
| 4,286,599 | 9/1981 | Hahn et al. | 81/9.22 |

FOREIGN PATENT DOCUMENTS

| 4669 | 10/1979 | European Pat. Off. . | |
|---|---|---|---|
| 6395 | 1/1980 | European Pat. Off. . | |
| 86515 | 7/1895 | Fed. Rep. of Germany . | |
| 110725 | 5/1900 | Fed. Rep. of Germany | 81/9.22 |
| 1133709 | 4/1957 | France . | |
| 7202657 | 9/1972 | Netherlands . | |
| 7302838 | 9/1973 | Netherlands . | |
| 1278461 | 6/1972 | United Kingdom . | |

Primary Examiner—Michael H. Thaler
Attorney, Agent, or Firm—Andrus, Sceales, Starke & Sawall

[57] ABSTRACT

A tatooing apparatus is provided with at least one needle carrier (17, 42, 47) with an arrangement of needles (19, 44, 46) by which at least a number of the needles are mutually arranged according to a program of symbols and in such a manner that the tissue to be tattooed can be pierced by the free ends of the needles. Each of the needles is hollow and is provided with an outlet opening close to its free end for feeding a contrasting fluid into the perforation in the tissue. The apparatus is further provided with a fluid feeding mechanism a control mechanism therefore, the fluid feeding mechanism comprising a reservoir (16, 43, 54) accommodating contrasting fluid and a program carrier of non-porous material, the program carrier also including perforations (30, 49) which are directed in relation to the inlet openings of the needles.

35 Claims, 10 Drawing Figures

TATTOOING APPARATUS

The invention relates to tattooing apparatus provided with at least one needle carrier which carries a plurality of needles and with operating means through which at least a number needles are mutually arranged according to a program of a symbol in such a manner that a tissue to be tattooed can be pierced by the free ends of the needles so that a number of perforations exist in the tissue and which perforations, after the feeding of a contrasting fluid thereto, assume the form of a tattoo in accordance with the programmed symbol.

Tattooing apparatus of this type is generally known and is used, amongst other purposes, for tattooing animals such as pigs, dogs and cats. By tattooing the ears of these animals they may be easily identified. In these known types of apparatus, supply of fluid to the needles is always carried out as a separate operation after perforation of the tissue has taken place. In order to achieve good dosing of the fluid a high degree of manual skill is needed.

The object of the invention is to provide a tattooing apparatus by which means a tattoo can be applied to a tissue in a simple and rapid manner in one continuous operation.

According to the invention, this is achieved by the fact that each of the needles is hollow and is provided with an outlet orifice in the region of its free end for feeding the contrasting fluid to the perforation in the tissue, and that fluid-flow controlling means are included in the operating means which comprise a reservoir for the contrasting fluid and a program carrier in which a number of perforations are arranged therein which are connected to the reservoir and are aligned with the inlet orifices of the needles.

In applying this invention for use, the contrasting fluid is fed in one operation following the perforation of the tissue for each tattoo and whereby the operating means effects feeding of the contrasting fluid as well as perforation. The use of a programmed carrier co-operatively arranged with respect to the fluid supply means to the needles can effect a substantial saving of time in preparing to carry out the tattooing. Thus a large number of animals can be tattooed in a short space of time with the apparatus according to the invention.

According to a preferred embodiment of the invention the program carrier is constituted by a perforated program plate which is withdrawably exchangeable in order to permit different symbols to be tattooed by the apparatus. The use of these withdrawably exchangeable program plates permit rapid setting-up of the symbols to be tattooed. In connection herewith, it is an advantage if the program plate and the reservoir are integral and that the reservoir includes at least one elastically deformable wall. By adapting the volume of the reservoir to accommodate the amount of fluid required for a tattooing operation no special attention need to be paid to the dosing of the fluid. Moreover by manufacturing the reservoir as a product for one-time use, only the required amount of fluid is stored in the reservoir to effect tattooing of a selected symbol or selected group of symbols. A favourable sealing-off effect on the perforations is obtained if the perforations in the program carrier are sealed off with a non-porous foil.

According to another preferred embodiment of the apparatus according to the invention, the reservoir is affixedly connected to the needles. Through such an arrangement both the setting-up procedure for and carrying out of tattooing is extremely simplified. An integrated unit comprising reservoir, program plate and needles lends itself particularly to mass-production methods through which a relatively low price is possible.

In the foregoingly quoted known types of apparatus the operating means is constituted by tattooing pliers comprising a jaw affixed to each of two arms thereof and the first jaw of which accommodates a counterpressure plate and the second jaw of which accommodates a pressure-plate connectable to the needle-carrier. A preferred embodiment of the apparatus according to present invention is characterised by fact that the pliers also include a pressure element which is movable with respect to the needles and the second jaw from a rest position in which no pressure is exercised on the fluid reservoir, and to a working position at which, after the needles have been driven into the tissue, pressure is exerted on the fluid reservoir to cause the fluid feeding means to press the fluid through the needles into the tissue to be tattooed. Through this arrangement, and after the needles have effected perforation of the tissue, feeding of the fluid follows immediately under optimal conditions without the need for a high degree of manual skill on the part of the person carrying out the tattooing operation.

A favourably operating embodiment of the apparatus according to the invention is obtained if the jaws are mutually constrained to move along a substantially straight line with respect to one another. Through such an arrangement, perforation of the tissue can take place in a straight line under optimal conditions.

The invention is now to be described with reference to the accompanying drawings which include examples of embodiments of the invention and in which.

Figures 1, 2:
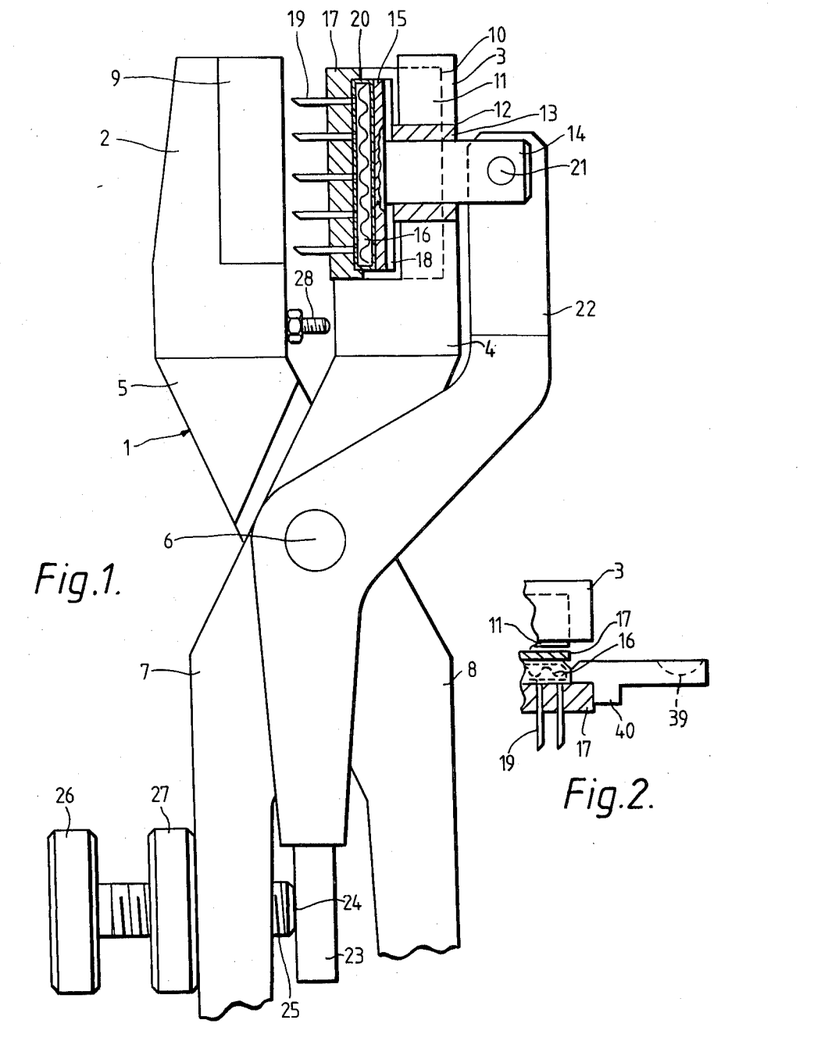
FIG. 1 shows a part of the tattooing apparatus according to the invention in partial side-elevation and partial cross-section.
FIG. 2 shows a part of the apparatus as shown in FIG. 1 and in partial side-elevation and in partial cross-section.

The tattooing apparatus illustrated in FIGS. 1 and 2 comprises a pair of tattooing pliers provided with jaws 2 and 3 which are affixed to the operating arms 5 and 4 respectively, these arms 4 and 5 are pivotably mounted for movement with respect to one another on the hinge-pin 6 and the free extremities 7 and 8 of which arms constitute handgrips.

The jaw 2 carries a block 9 of relatively hard rubber on the inner side thereof and which block forms a counter-pressure plate against which there can lay the tissue forming part of the ear of a pig, sheep, dog or other animal for example. On the inner side of the jaw 3 lying opposite the jaw 2, a recess 10 is incorporated and which recess accommodates a pressure-plate 11. A hole 12 running through the jaw 3 and the pressure-plate 11 affixedly accommodates a bush 13 therein. A pressure-applying pin 14 is slidably accommodated in and extends from the bush 13 for movement with respect thereto. The pressure-applying pin 14 is provided with a flat platelike pressure element 15 affixed thereto and on the side thereof extending from the jaw 3. This pressure element can exercise pressure on the fluid reservoir 16 which is accommodated in the recess 18 together with the pressure element 15 and these members are enclosed within the needle carrier 17 and the pressure-plate 11.

The needle carrier 17 carries a plurality of hollow needles 19 arranged in matrix form and which can receive fluid from the fluid reservoir 16 in a manner later to be described herein. It is also possible for the needle carrier 17 to carry a particular arrangement of needles 19. The outer peripheral edge 20 of the needle carrier 17 can be subjected to pressure by the pressure-plate 11, whilst the reservoir 16 can be subjected to pressure by the pressure element 15 separately and independently of the pressure applied to needle carrier 17. The end of the pressure-applying pin 14 extends from the jaw 3 and operates via a hingepin 21 together with the end of the additional operating arm 22 which is also pivotably hinged on the hingepin 6. The additional operating arm 22 is also fitted with a platelike stop 23 on the other end portion thereof with respect of the hingepin 6. This stop member 23 can abut against a stop constituted by the end surface 24 of an adjusting screw 25 which is provided with an operating knob 26 and accommodates a locking nut 27 thereon.

Through the adjustment of the adjusting screw 25, the instant at which the pressure-applying pin 14 is coupled to the stop 24 can be determined. As the result of this coupling the pressure element is moved from its rest position, in which it exercises no pressure applying influence on the fluid reservoir 16, to its operating position in which the pressure element can apply pressure to the reservoir 16.

An adjustable stop screw 28 is arranged between the jaws 2 and 3 and with a threaded end thereof engaging in a tapped hole in the jaw 2. The amount of open distance existing between the jaws can be fixed by adjustment of this stop screw 28.

Figure 3:
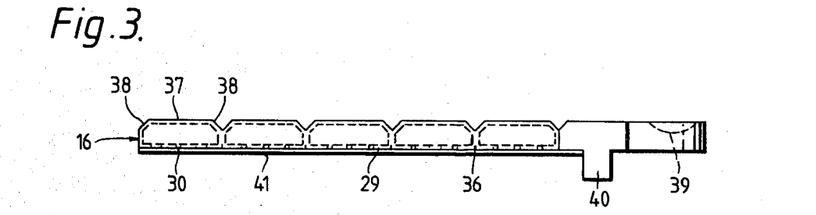
FIG. 3 shows a side-elevation of a program carrier and fluid reservoir which is applicable for use in the apparatus according to FIG. 1.
Figure 4:
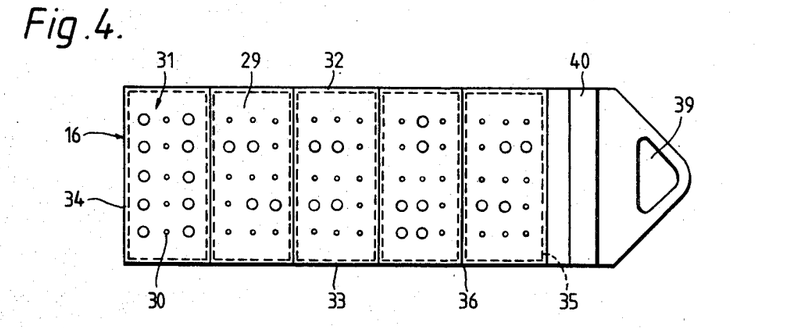
FIG. 4 shows the underside of the program carrier according to FIG. 3.

As shown in FIGS. 3 and 4, the reservoir 16 is united with a program carrier or program plate 29 to form the bottom of the reservoir 16 and can be manufactured from a non-porous material through which a number of perforations 30 extend. These perforations 30 are arranged within a matrix of a number of matrices 31 of perforation positions and through which the program of symbols can be set up. In FIG. 4, the program consists of a five-cipher number—12345, however it will be clear that other combinations such of ciphers and/or letters and/or other symbols can be formed by perforations. It is emphasised here that in addition to the five-cipher combination of symbols illustrated it is equally possible to program in other numbers of symbol combinations or a single symbol.

The reservoir 16 further comprises longitudinally-running side walls 32 and 33 and transversely-running side walls 34 and 35. The reservoir 16 is preferably divided into compartments by the inclusion of partitions 36. The upper side of the reservoir 16 is covered off with an upper wall 37 having elastically deformable walls 38 which are slopingly arranged. A handgrip 39 is arranged on the transverse wall 35, and by means of which the program carrier can be easily withdrawn or inserted into the pliers for effecting a change of program. An extending edge of a stop 40 serves to effect positioning of the program carrier with respect to the pliers 1. The program carrier with the fluid reservoir can be efficiently manufactured from synthetic material and through which the carrier can be made in one piece initially without the upper wall 37 and, following this, can be provided with appropriate symbol perforations in a perforating device (not shown); and whereafter a preferably self-adhering foil 41 is affixed to the underside of the program plate 29. Hereon and within the reservoir 16 contrasting fluid is accommodated and which fluid is preferably in the form of a paste and substantially sufficient in quantity to carry out one tattooing operation. After filling with the fluid, the upper wall 37 can be (thermally) welded to the program carrier 29 and the element is ready for use.

By the use of this program carrier 29 with the fluid reservoir according to the invention, the foil 41 can be removed before the perforating operation and be affixed to a card for example of a card system utilised for administrational purposes. It is also possible that, by manufacturing the foil 41 from a cellophane which is unharmful to animals, the foil remains adhering to the plate 29 and is pierced by the extending inlet openings in the needles 19.

By sliding the program carrier 29, with the fluid reservior 16, into the recess 18 of the pliers 1 until the stop edge 40 of the program carrier 29 is engaged, the program carrier is located in its correct position for operation. This positioning operation results in the perforations 30 being aligned in relation to the inlet openings of a number of needles 19 so that the reservoir and the carrier that together form the means for feeding the fluid are enabled to feed a selected number of needles 19 with the fluid.

After the needles 19 have pierced through the tissue through the movement of operating arms 4 and 5 toward one another, with further movement of the operating arms, the pressure element 15 will be moved from its rest position to its operating position and whereupon the pressure element 15 will exert pressure on the upper wall 37 and the fluid pushed in the reservoir will be pushed out via the perforations 30 and through which the fluid will be fed to the perforations in the tissue via the extending inlet openings and the associated free ends of the selected needles. In this manner tattooing will be carried out in accordance with the pattern of programmed symbols in the needle carrier 17.

It should be noted here that the needles 19 preferably have a length which is such that they perforate the tissue to a sufficient depth in order to ensure that the contrasting fluid fed thereto remains retained by the tissue, and such that a clearly visible tattoo remains after the passing of time.

In the foregoingly described embodiment, perforations were made in the tissue by all the needles 19 in the needle carrier 17, and thereafter only those of the needles programmed to form symbols by the program carrier 29 fed fluid to the perforations made in the tissue by these needles. Those of the needle pierced perforations in the tissue, which are not fed with fluid, seal themselves off after some time and thus have no influence on the pattern of the tattoo.

Figure 5:
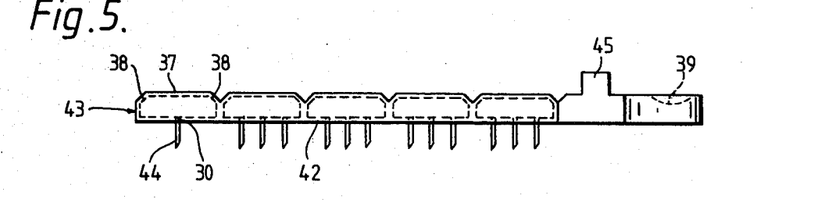
FIG. 5 shows a side-elevation of a second embodiment of a program carrier with a fluid reservoir.
Figure 6:
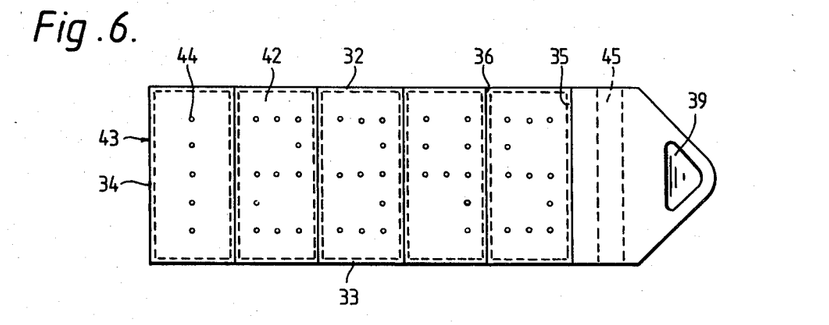
FIG. 6 shows the underside of the program carrier according to FIG. 5.

In a following embodiment illustrated in FIGS. 5 and 6 a program carrier or program plate 42 is used and which plate forms the program carrier 29 and the bottom of a reservoir 43. The program carrier is however directly connected to the perforations by a number of needles 44 which have been set up according to a programmed symbol, or according to a number of programmed symbols. The program carrier 42, is manufactured integrally with the needles 44 as a one-piece assembly and thus also performs the function of a needle carrier. In this particular embodiment, a stop edge 45 is arranged on the side of the reservoir 43 remote from the needles in order that it may co-act with the jaw 3. In this example of an embodiment of the invention, the design is preferably such that a pressure plate 11 is provided in order to peripherally grip the edges of the reservoir in a manner not shown, and so that the pressure applied to the needles 44 by the pressure plate can be exercised without influencing the pressure on the fluid accommodated in the reservoir. The other parts of the reservoir correspond at least in the main to those of the reservoir 16 and are indicated by the same reference numerals shown therefor.

The contrasting fluid applied, preferentially ink in paste form, is of great advantage when used with this embodiment insofar that with it's high viscosity and with the use of small needle diameters no special closure means for the program carrier 42 is necessary. Preferably, the paste should be of such a composition that it is not prone to drying up.

The program carrier 42, the reservoir 43 and the needle carrier 44 should be integrally manufactured to provide a one-time usable entity which can be thrown away after use. In this manner infection can be prevented and the programmed combination of symbols in the program carrier can be used only once.

Figure 7:
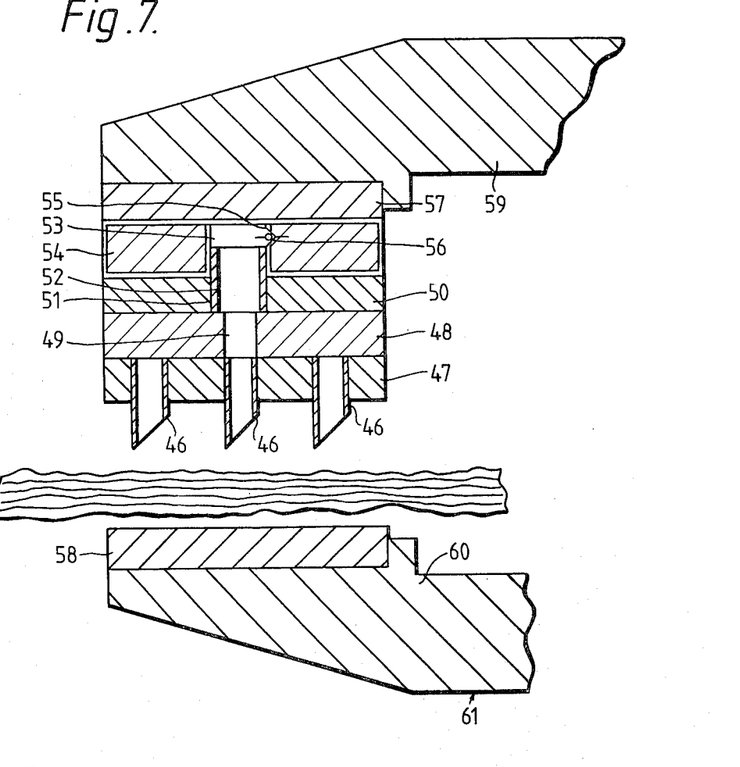
FIG. 7 shows a part of another embodiment of the tattooing apparatus according to the invention, and in partial side-elevation and in partial cross-section.

The embodiment illustrated in FIG. 7 shows a plurality of needles 46 affixed to a plate-like needle carrier 47 which can be manufactured from a synthetic material or rubber and in which the needles have been affixed thereto in a sealed-off manner. As in the first described embodiment, the needles are set in matrix form and in such a manner that all desired symbols can be desired therefrom. A program carrier or plate 48 is provided with perforations which extend to the inlet openings of a number of needles 46. The program plate 48 can, according to requirements therefor, have the symbols to be tattooed altered and through which the concerned needles 46 are either fed with fluid or not.

A fluid-feed plate 50 is arranged against the program plate 48 on the side thereof remote from the needle carrier, and which fluid-feed plate 50 is preferably composed of a soft and compressible material such as a foam substance for example and preferably having closed cells. A number of perforations 51 are also to be found in the fluid-feed plate 50 and along the axes of which perforations 51 fluid-carrying tubes 52 are affixed. The tubes are longer than the thickness of the fluid-feed plate 50 and each of which extends into a channel 53 of a fluid reservoir 54 located on the side thereof remote from the program plate 48. Each of the channels 53 of the reservoir 54 is provided with a closed wall in which a schematically illustrated non-return valve 56 is arranged and which permits the fluid to be injected into the perforated tissue from the reservoir 54 via the tube 52, the perforation 49 and the hole of the needle. The needle carrier 47 and fluid-feed means assembly comprising the program plate 48, the fluid-feed plate 50 and the fluid reservoir 54 is connected, in a manner not shown, to the pressure plate 57 which lies against the reservoir. It is preferred that all these elements comprising this assembly be arranged in such a manner that they are exchangeable.

The compressive action, necessary for the injection of the quantity of fluid into the perforation in the tissue, is generated through the aid of the pressure plate 57 by which means force is applied to the assembly arranged thereagainst. At the same time, and in equal magnitude, a counter pressure is preferably exercised by a counter-pressure plate 58 which is located on the other side of the tissue to be tattooed. To this end, plates 57 and 58 are preferably affixed to operating means in the form of the jaws 59 and 60 of pliers 61, and through which the necessary force required to effect perforation and control of the fluid need only to be slight.

As with the first embodiment, and in a manner not shown, it is possible with this embodiment to exercise pressure separately on the needle carrier 47 and the reservoir 54. To this end the plate 57 is replaced by a pressure plate acting directly on the needle carrier to apply pressure thereto and a separately operable pressure element lying against the reservoir is provided whereby operation is accomplished in the same manner as that for the first embodiment.

The tattooing apparatus according to FIG. 7 offers the facility of optimal exchangability of the various elements of the assembly. Through this, good adaption to the symbols to be tattooed is achieved at the same time as good adaption to the nature of the tissue to be tattooed is possible.

Figure 8:
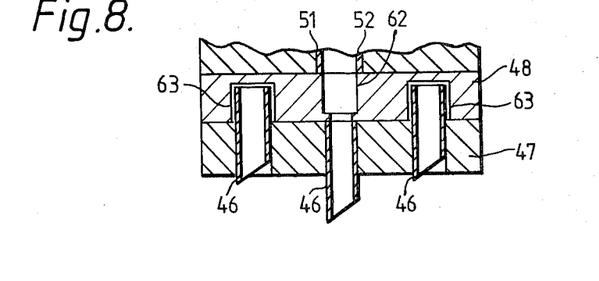
FIG. 8 shows a cross-section of yet another embodiment of the apparatus according to the invention.

Under certain circumstances, it may be desired not to perforate tissue with all of the needles 46. To this end and as shown in FIG. 8 of another embodiment, the program plate 48 also comprises recesses 63 alongside perforations 62 and into which the unprogrammed needles can sink. Thus the program plate selects a number needles set up in accordance with the desired symbols and renders the remaining needles inoperable.

Figures 9, 10:
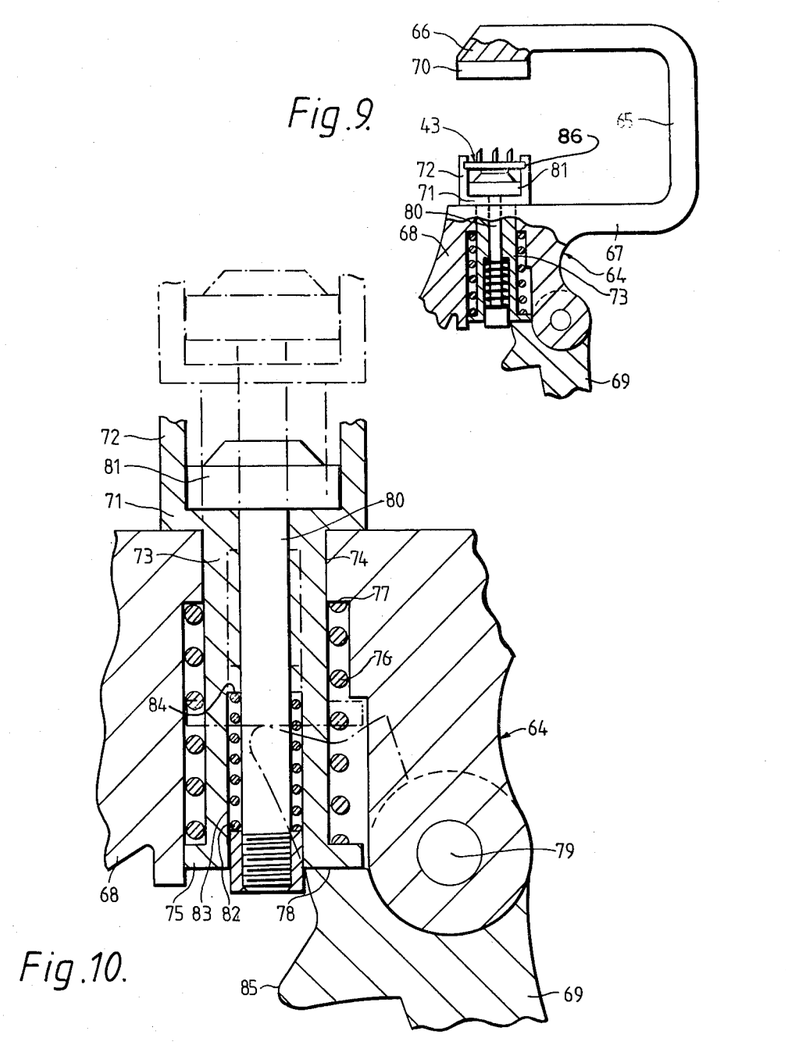
FIG. 9 shows a part of yet another embodiment of the apparatus according to the invention, and in partial side-elevation and cross-section.
FIG. 10 shows the apparatus according to FIG. 9 on a larger scale.

The embodiments illustrated in FIGS. 9 and 10 comprise the tattooing apparatus and tattooing pliers 64 with operating means constituted by a carrier arm 65 which is substantially of 'U' form, and outer and inner legs 66 and 67 respectively. On its side lying opposite the outer leg 66, the inner leg 67 carries a fixed operating arm 68 which slopes at an acute angle, and another hinged operating arm 69 also sloping at an acute angle. The free end of the outer leg 66 forms a fixed first jaw which carries a counter-pressure plate 70, whilst a second movable jaw 71 is arranged on the inner side of the leg 67. The second jaw 71 carries a pressure plate 72 and is displacable with the aid of the operating pin 73 which extends through a guide-hole 74 in the operating arm 68.

The operating pin 73 is fittingly accommodated in a restricted portion of guide-hole 74 and is exteriorially provided with an extending collar 75 at one end. A compression spring 76 is accommodated on the operating pin 73, and which compression spring is located in a portion of the guide-hole 74 of larger diameter. This portion serves as a receiving chamber for the compression spring 76 and through which the upper end of the compression spring locates against a shoulder 77 in the receiving chamber and the lower end locates against the inner side of the collar 75. A first operating lug 78, which is affixed to the operating arm 69 which is pivotable in relation to the arm 68 on hingepin 79, locates against the free surface of the collar 75. A pressure pin 80 is co-axially accommodated within the operating pin 73 for the purpose of operating a punch or pressure element 81 located within the second jaw 71. Likewise, the pressure pin 80 carries a compression spring 82 which is accommodated in a diametrically enlarged portion of a hole 83 and locates against a collar 84 on the pressure pin 80. The end of the pressure pin 80, remote from the pressure element 80, co-acts with the operating arm 69 after the operating lug 78 has engaged the operating pin 73, and due to the fact that a second operating lug 85 acting as a stop and connecting with the first operating lug 78 has engaged with the operating pin.

The second pressure plate 72 has a pair of grooves 86 into which the unit comprising the program carrier and reservoir according to FIGS. 5 and 6 is easily introducable. Through the operation of the pliers 64, and in a manner described with reference to the first embodiment, the needles are caused to pierce the tissue by the action of the second jaw 71, and whereafter the pressure element 81 exercises pressure on the reservoir which then feeds the fluid to the perforations in the tissue.

Through the manner in which the pliers 64 have been designed, the jaws 66 and 71 can be moved mutually along a substantially straight line i.e. parallel motion therebetween, and through which action the jaw 66 remains relatively stationary and the jaw 71 can be moved in a substantially straight line between the rest position and the operating position at which pressure is exerted on the needles to perform their functions. A relative movement such as this in a substantially straight line between the rest position and the operating position at which pressure is exerted on the needles to perform their functions. A relative movement such as this in a substantially straight line is particularly favourable in the interests of achieving perforation of the tissue by the needles at right angles thereto. The pressure element 81 also moves along a straight line between the rest position and the operating position, an action which is an advantage in the interests of building up a fluid pressure in the reservoir and which pressure is distributed as evenly as possible.

The invention is not restricted to the embodiments described and in its scope embraces the possibilities of producing other variations thereof.

What we claim is:

1. Tattooing apparatus for marking animals by the injection of a contrasting fluid into tissue of the animal, said apparatus comprising:
    a needle carrier;
    a plurality of hollow needles carried by said needle carrier, said needles being arranged in a matrix capable of forming marking symbols from combinations of selected ones of said needles, each of said needles having an inlet orifice at a first end and an outlet orifice at a second, free end;
    at least one reservoir for the contrasting fluid;
    a marking symbol program carrier exchangeably mounted in said apparatus intermediate said needles and said reservoir, said program carrier having a plurality of fluid channels arranged in a marking symbol pattern and forming an animal marking symbol, each of said fluid channels of said plurality being separately alignable with one of said selected ones of said needles when said program carrier is mounted in said apparatus for connecting said reservoir and said inlet orifices of said selected ones of said needles; and
    operating means for inserting at least said selected ones of said needles in the tissue of the animal to be marked and for flowing fluid from said reservoir through said selected ones of said needles for injection into the tissue from the outlet orifices of said selected ones of said needles for marking the animal with the symbol of the program carrier.

2. The tattooing apparatus according to claim 1 wherein said apparatus is so formed as to insert all needles into the tissue of the animal to be marked.

3. The tattooing apparatus according to claim 1 wherein said apparatus is so formed as to insert said selected ones of said needles into the tissue of the animal to be marked.

4. The tattooing apparatus according to claim 3 wherein said needles are axially movable in said carrier, and wherein said program carrier has abutments surrounding said fluid channels communicating with said selected ones of said needles for establishing said needles in a position extended with respect to said needle carrier, and wherein said needle carrier has recesses for allowing needles other than said selected ones to be retracted into said needle carrier.

5. The tattooing apparatus according to claim 4 wherein said program carrier has recesses for allowing retraction of needles other than said selected ones.

6. The tattooing apparatus according to claim 1 wherein said program carrier and reservoir are formed as an integral unit.

7. The tattooing apparatus according to claim 1 or 6 wherein said matrix for the needles in said needle carrier and said pattern for the fluid channels in said program carrier are substantially identical.

8. The tattooing apparatus according to claim 1 or 6 wherein said needle carrier and program carrier contain a plurality of needle matrices and fluid passage patterns, respectively.

9. The tattooing apparatus according to claim 1 or 6 wherein said reservoir contains a quantity of fluid sufficient for a single tattooing injection.

10. The tattooing apparatus according to claim 1 wherein said contrasting fluid in said reservoir is paste-like in form.

11. The tattooing apparatus according to claim 1 or 6 wherein said program carrier includes means for establishing the alignment of said fluid channels with said selected ones of said needles.

12. The tattooing apparatus according to claim 1 or 6 wherein said program carrier includes a grip suitable for grasping to mount or dismount the program carrier in the apparatus.

13. The tattooing apparatus according to claim 1 wherein said program carrier has a film-like member for sealing said fluid channels.

14. The tattooing apparatus according to claim 13 wherein said film-like member is provided with a self-adhering layer on the program carrier side thereof.

15. The tattooing apparatus according to claim 1 wherein said operating means includes first and second opposing jaws movable toward and away from each other by said operating means, said first jaw comprising a counter pressure plate, said second jaw having said needle carrier, program carrier, and reservoir mounted thereon, said second jaw being movable between a rest position away from said first jaw and a working position in proximity to said first jaw and in which needles are inserted in animal tissue placed between said jaws and fluid from said reservoir injected therein.

16. The tattooing apparatus according to claim 15 wherein said second jaw has a pressure element coacting with said reservoir and relatively movable with respect to said second jaw for applying pressure to said reservoir to flow fluid through selected ones of said needles.

17. The tattooing apparatus according to claim 15 wherein said operating means is so formed that said pressure element becomes operable to apply pressure to said reservoir upon a preselected amount of movement of said second jaw toward said first jaw.

18. The apparatus according to claim 15 or 16 wherein said operating means is generally in the form of a pair of pliers having a pair of pivotally mounted operating arms containing said first and second opposing jaws at one end thereof and means for operating said arms at the other end thereof.

19. The tattooing apparatus according to claims 15 or 16 wherein said operating means is so formed as to move said first and second jaws toward and away from each other along a substantially straight line.

20. The tattooing apparatus according to claim 16 wherein said operating means is so formed as to move said first and second jaws toward and away from each other along a first substantially straight line and wherein said pressure element moves with respect to said second jaw along a second substantially straight line parallel to said first line.

21. An exchangeable, marking symbol program carrier for animal tattooing apparatus having a plurality of hollow needles arranged in a matrix capable of forming marking symbols from combinations of selected ones of said needles and having an operating means for inserting needles in the tissue of the animal to be marked and injecting contrasting fluid therein, said program carrier comprising:
  a member exchangeably mountable in the apparatus and having a plurality of fluid channels arranged in a marking symbol pattern and forming an animal marking symbol, each of said fluid channels being separately alignable with one of said selected ones of the needles when the program carrier is mounted in the apparatus for providing a fluid path for the contrasting fluid to the selected ones of the needles; and
  a reservoir for the contrasting fluid formed as an integral unit with said member for providing contrasting fluid to said fluid channels of said member.

22. The program carrier according to claim 21 wherein the pattern for the fluid channels in said program carrier member is substantially identical to the matrix for the needles in the tattooing apparatus.

23. The program carrier according to claim 21 suitable for use with tattooing apparatus in which the needles are axially movable, said program carrier having abutments surrounding said fluid channels communicating with the selected ones of said needles for establishing these needles in an extended position.

24. The program carrier according to claim 23 wherein said program carrier has recesses for allowing needles other than the selected ones to assume a retracted position.

25. The program carrier according to claim 21 wherein said reservoir contains a quantity of fluid sufficient for a single tattooing injection.

26. The program carrier according to claim 25 wherein said contrasting fluid in said reservior is paste-like in form.

27. The program carrier according to claim 21 wherein said program carrier member includes means for establishing the alignment of said fluid channels with the selected ones of the needles when the member is mounted in the apparatus.

28. The program carrier according to claim 21 wherein said program carrier member includes a grip suitable for grasping to mount or dismount the program carrier in the apparatus.

29. The program carrier according to claim 21 wherein said program carrier member has a film-like member for sealing said fluid channels.

30. The program carrier according to claim 29 wherein said film-like member is provided with a self-adhering layer on the program carrier member side thereof.

31. A tool for tattooing apparatus having a plurality of needles mounted in a needle carrier and arranged in a matrix capable of forming marking symbols from combinations of selected ones of the needles, a reservoir for contrasting fluid, and a marking symbol program carrier having a plurality of fluid channels arranged in a pattern and forming an animal marking symbol, said channels connecting said reservoir to selected ones of said needles, said tool having:
  first and second opposing jaws; said first jaw comprising a counter pressure plate; said second jaw being formed to mount the needle carrier thereon, said second jaw having a a pair of opposing grooves in which the reservoir and program carrier are exchangeably mountable in operative association with the needle carrier, said second jaw including positioning means coactable with the program carrier for obtaining alignment of the fluid channels of the program carrier with selected ones of the needles and the connection of selected ones of the needles to the reservoir, said second jaw having a pressure element coactable with the reservoir and relatively movable with respect to said second jaw for applying pressure to said reservoir to flow fluid through selected ones of the needles; and
  actuating means for moving said second jaw between a rest position away from said first jaw and a working position in proximity to said first jaw and in which the needles are inserted in animal tissue placed between said jaws and fluid from the reservior injected therein.

32. The tool according to claim 31 wherein said tool is so formed that said pressure element becomes operable to coact with the reservoir upon a preselected amount of movement of said second jaw toward said first jaw.

33. The tool according to claim 31 wherein said tool is generally in the form of a pair of pliers having a pair of operating arms pivotally joined at a common pivot point, said operating arms containing said first and second jaws at one end thereof and means for actuating said arms at the other end thereof.

34. The tool according to claim 33 wherein said pressure element is mounted on a third operating arm pivotally mounted on the common pivot point of said pair of operating arms and wherein one of said first and second arms includes a stop mechanism coacting with said third operating arm for effecting the relative movement of said pressure element.

35. The tool according to claim 34 wherein said tool is so formed as to move said first and second jaws toward and away from each other along a first substantially straight line and wherein said pressure element moves with respect to said second jaw along a second substantially straight line parallel to said first line.

* * * * *